United States Patent [19]

Fehr et al.

[11] Patent Number: 4,990,496
[45] Date of Patent: Feb. 5, 1991

[54] USE OF CYCLOALIPHATIC KETONES AS PERFUMING AND FLAVORING INGREDIENTS

[75] Inventors: Charles Fehr, Versoix; José Galindo, Les Avanchets, both of Switzerland

[73] Assignee: Firmenich S.A., Geneva, Switzerland

[21] Appl. No.: 305,815

[22] Filed: Feb. 3, 1989

[30] Foreign Application Priority Data

Feb. 5, 1988 [CH] Switzerland .......................... 418/88
Sep. 15, 1988 [CH] Switzerland .......................... 3441/88

[51] Int. Cl.$^5$ ............................................. A61K 7/46
[52] U.S. Cl. .................................. 512/24; 252/174.11;
252/8.6; 426/538; 424/76.4; 131/276
[58] Field of Search ................... 512/24; 252/174.11,
252/86; 568/378; 426/538; 424/76.4; 131/276

[56] References Cited

U.S. PATENT DOCUMENTS

| 3,956,392 | 5/1976 | de Haan et al. ................... 568/378 |
| 4,136,066 | 1/1979 | de Haan et al. ................... 568/378 |
| 4,198,309 | 4/1980 | Mookherjee ...................... 568/378 |
| 4,210,553 | 7/1980 | Trenkle et al. ................... 568/378 |
| 4,217,252 | 8/1980 | Trenkle et al. ................... 568/378 |

FOREIGN PATENT DOCUMENTS 50-69047  6/1975  Japan .............................. 512/24

OTHER PUBLICATIONS

Ohloff et al, Helv-Chim. Acta., vol. 53, p. 531 (1970).

Primary Examiner—James H. Reamer
Attorney, Agent, or Firm—Pennie & Edmonds

[57] ABSTRACT

Optically active isomers of alpha-damascone of formula

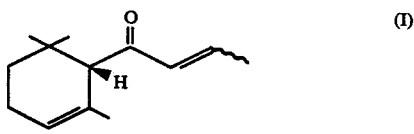

wherein the wavy line designates a C—C bond of cis or trans configuration and its 3-buten-1-one derivative are new compounds having utility in the perfume and flavor industry. They can be prepared starting from an enolate of formula

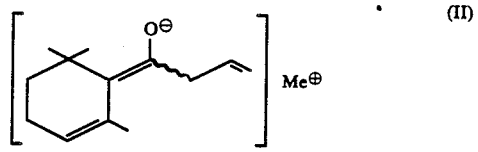

where the wavy line has the meaning given above and Me designates an alkali metal, preferably lithium or magnesium, by treating said enolate with a bifunctional nitrogen derivative of formula

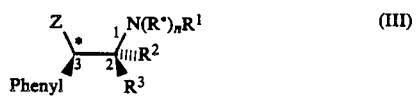

where
the asterisk identifies a center of chirality;
index n stands for zero or 1;
each of symbols $R^0$ and $R^1$ defines a linear or branched alkyl or aralkyl radical, or one of them represents a hydrogen atom and the other an alkyl radical as defined above;
each of symbols $R^2$ and $R^3$ represents a linear or branched alkyl radical, or one of them represents a hydrogen atom and the other an alkyl such as defined above; and
Z designates an OH group or a divalent radical of formula HN-C(O), the nitrogen atom of which is bound to the carbon atom at position 3 and the carbonyl group is bound to the nitrogen atom at position 1;
and wherein the nitrogen atom at position 1 can be optionally bound to a benzylic group of a polystyrenic resin; hydrolyzing the reaction mixture and isomerizing it by means of an isomerization agent.

Cycloaliphatic ketones (I) are also prepared starting from an organo-magnesium compound of formula

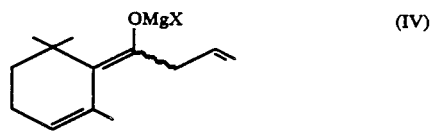

where the wavy line has the above given meaning and X designates a halogen atom, by treating said compound with one equivalent of a lithium alkoxide.

15 Claims, No Drawings

USE OF CYCLOALIPHATIC KETONES AS PERFUMING AND FLAVORING INGREDIENTS

BRIEF SUMMARY OF THE INVENTION

The present invention relates to (—)-(1S)-1-(2',2',6'-trimethyl-2'-cyclohexen-1'-yl)-2-buten-1-one and (—)-(1S)-(2',2',6'-trimethyl-2'-cyclohexen-1'-yl)-3-buten-1-one. This invention relates also to the utilization of (—)-(1S)-1-(2',2',6'-trimethyl-2'-cyclohexen-1'-yl)-2-buten-1-one as a perfuming and flavoring ingredient in the preparation of perfume, perfume bases, perfumed products and in the aromatization of edible material.

The present invention provides further a process for the preparation of (—)-(1S)-1-(2',2',6'-trimethyl-2'-cyclohexen-1'-yl)-2-buten-1-one of formula

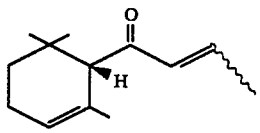

(I)

wherein the wavy line designates a C—C bond of cis or trans configuration, which process comprises the steps of
a. treating an enolate of formula

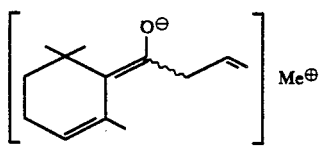

(II)

where the wavy line has the meaning given above and Me designates an alkali metal, preferably lithium or magnesium, with a proton donating chiral reagent consisting of a bifunctional nitrogen derivative of formula

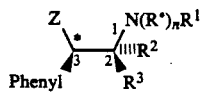

(III)

where
the asterisk identifies a center of chirality;
index n stands for zero of 1;
each of symbols R* and R¹ defines a linear or branched alkyl or aralkyl radical, or one of them represents a hydrogen atom and the other an alkyl radical as defined above;
each of symbols R² and R³ represents a linear or branched alkyl radical, or one of them represents a hydrogen atom and the other an alkyl such as defined above; and
Z designates an OH group or a divalent radical of formula HN-C(O), the nitrogen atom of which is bound to the carbon atom at position 3 and the carbonyl group is bound to the nitrogen atom at position 1;
and wherein the nitrogen atom at position 1 can be optionally bound to a benzylic group of a polystyrenic resin;
b. hydrolyzing the reaction mixture to give (—)-(1S)-(2',2',6'-trimethyl-2'-cyclohexen-1'-yl)-3-buten-1-one, and c. isomerizing it by means of an isomerization agent.

This invention provides further a process for the preparation of (—)-(1S)-1-(2',2',6'-trimethyl-2'-cyclohexen-1'-yl)-2-buten-1-one, which process comprises the following subsequent steps:
a. treating an organo-magnesium compound of formula

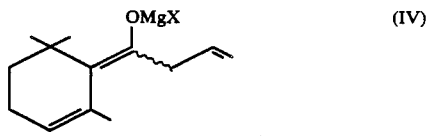

(IV)

where the wavy line designates a C—C bond of cis or trans configuration and X designates a halogen atom, with one equivalent at least of a lithium alkoxide;
b. adding to the reaction mixture one equivalent at least of a proton donating chiral reagent consisting of a bifunctional nitrogen derivative of formula (III) as defined above;
c. hydrolyzing the reaction mixture and isomerizing it by means of a current isomerizing agent; or
a'. treating an organo-magnesium compound of formula (IV) with one equivalent at least of a lithium alkoxide consisting of a lithium salt of a hydroxylic nitrogen compound of formula (III) as defined above;
b'. adding to the reaction mixture one equivalent at least of a proton donor consisting of an aliphatic alcohol, preferably tert-butanol; and
c'. hydrolyzing and isomerizing as indicated under letter c. above.

BACKGROUND OF THE INVENTION

The present invention relates to perfumery and to the flavor industry. It relates more particularly to optically active isomers of alpha-damascone, namely the enantiomer of formula

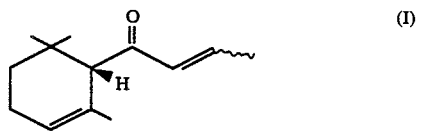

(I)

or (—)-(1S)-1-(2',2',6'-trimethyl-2'-cyclohexen-1'-yl)-2-buten-1-one and its -3-buten-1-one derivative.

Ever since their discovery [see Swiss Patents Nos. 509,399 and 524,320; Helv. Chim. Acta, 53, 541 (1970)], the interest encountered by damascones and their derivatives has been steadily growing among perfumers and flavorists. Their organoleptic qualities make them the ingredients of choice in a great variety of compositions destined to a wide range of applications. Their use streches from fine fragrances to the perfuming of household materials or toiletries such as soaps and detergents.

In particular, alpha-damascone has found a large utilization in fruity and floral type composition and its fragrance character of green apple type has enabled the creation of highly appreciated original olfactive notes.

Numerous publications have appeared reporting processes for its preparation. In most of the cases examined, however, these processes revert to the preparation of the racemic compound. alpha-Damascone in effect has been used so far in its racemic form.

G. Ohloff and G. Uhde [Helv. Chim. Acta, 53, 531 (1970)] have however described a process for the preparation of (R)-(+)-alpha-damascone, or (+)-(1'R,E)- and (+)-(1'R,Z)-1-(2',2',6'-trimethyl-2'-cyclohexen-1'-yl)-2-buten-1-one of formula

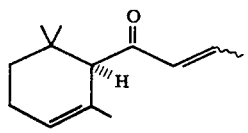

The process is characterized by an oxidation with manganese dioxide of the corresponding secondary alcohol which was obtained from (+)-alpha-ionone according to the following reaction scheme:

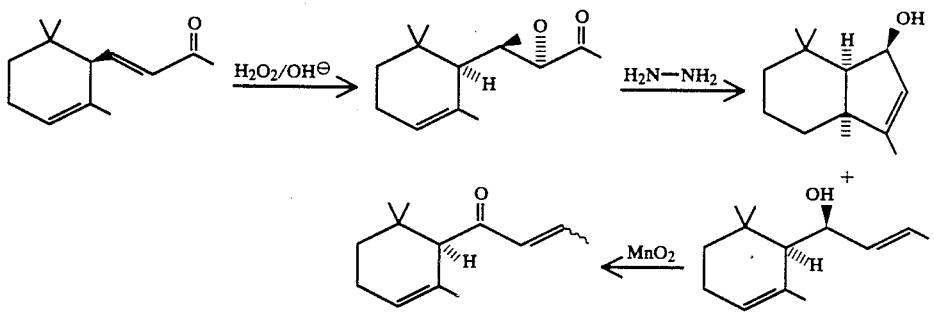

The compound thus obtained showed an $[\alpha]^{20}_D = +324°$ for the E form and $[\alpha]^{20}_D = +340°$ for isomer Z.

M. Shibasaki et al. [Chem. Pharm, Bull., 23, 279 (1975)] have also described a process for the synthesis of the same isomer of alpha-damascone, which process comprises the diastereomeric cyclization of citral by means of a chiral auxiliary reagent via the formation of its enamines, as indicated hereinbelow:

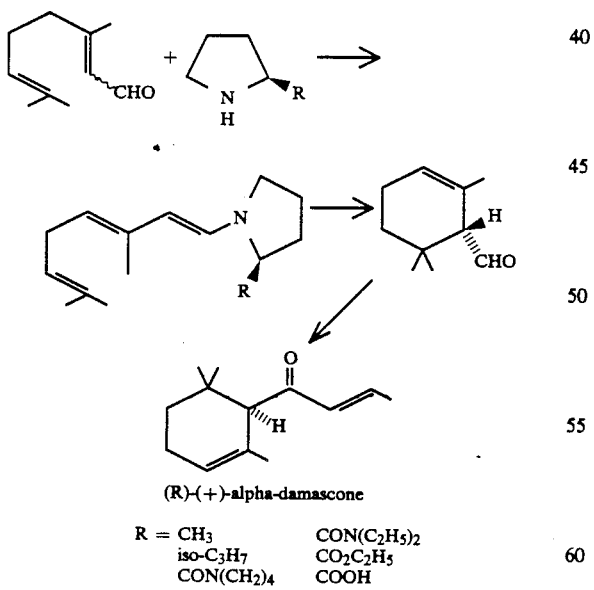

(R)-(+)-alpha-damascone

| R = CH₃ | CON(C₂H₅)₂ |
| iso-C₃H₇ | CO₂C₂H₅ |
| CON(CH₂)₄ | COOH |

By making reference to the values given by Ohloff and Uhde, the compound thus obtained by the cited authors possessed an optical purity of 27.5% and showed and $[\alpha]^{20}_D = +89.2°$.

We could establish that isomer (R)-(+) thus prepared, while possessing an olfative note characterized by a pleasant fruity and floral note, showed also a nuance which was reminiscent of "cork". This rendered its utilization somehow problematic.

This observation led us to examine the nature of the odor properties of the other enantiomer, (S)-(−)-alpha-damascone. Unfortunately, in the present state of our knowledge, we were not in the position to synthesize such an enantiomer lacking an appropriate synthetic method.

The present invention obviates this problem.

THE INVENTION

Suitable proton donating chiral reagents include preferably a hydroxy-amine of formula

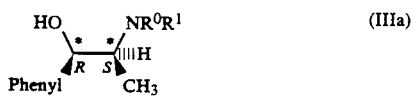
(IIIa)

Examples of hydroxy-amines (IIIa) are (1R,2S)-2-(methylamino)-1-phenylpropan-1-ol, or 1-ephedrine, (1R,2S)-2-(dimethylamino)-1-phenylpropan-1-ol, (1R,2S)-2-(isopropylamino)-1-phenylpropan-1-ol, (1R,2S)-2-(N-methyl-N-isopropyl-amino)-1-phenylpropan-1-ol, or a cyclic derivative of urea of formula

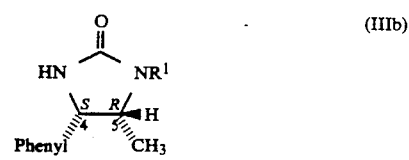
(IIIb)

for instance the compounds wherein $R^1 = CH_3$ or isopropyl.

The first class of reagents mentioned above belongs to the category of ephedrine derivatives compounds can be obtained either from ephedrine itself or from mandelic acid, both of which are readily available raw materials.

The reagents of the second type belong to the class of cyclic urea derivatives known in the art.

Thus, 1-2-(N-methyl-N-isopropylamino)-1-phenylpropan-1-ol can be obtained from 1-ephedrine by condensation with acetone in ethanol, followed by reduction with NaBH₄, whereas 1-2-(isopropylamino)-1-phenylpropan-1-ol is obtained by an analogous way from 1-norephedrine according to J. E. Saavedra [J. Org. Chem., 50, 2271 (1985)].

The other proton donating chiral reagents having analogous structure can be prepared according to similar synthetic methods.

To this class of chiral derivatives belong also the polymeric derivatives of known composition and described for instance by J. M. J. Fréchet et al., [J. Org. Chem., 51, 3462 (1986)]. They are polymeric resins wherein the nitrogen atom at position 1 of compounds (III) is bound to the p-methylene group of the aromatic radical of the resin.

Typically, these compounds include the derivatives of formula

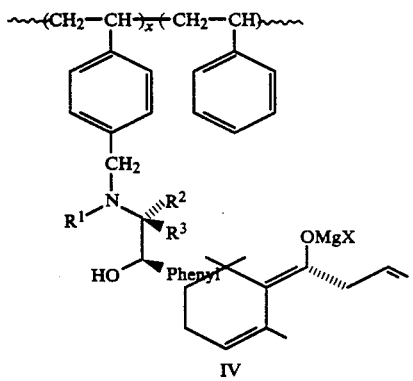

These reagents possess the considerable advantage of having the faculty of being easily regenerated by filtration.

With regard to the other class of reagents, viz. the cyclic urea derivatives, they can also be obtained by known processes. Thus, (+)-(4S,5R)-1,5-dimethyl-4-phenyl-2-imidazolidone can be obtained from (+)-ephedrine hydrochloride by reaction with urea ([alpha]$^{20}_D$= +44.5° (c=3; CH$_3$OH)) according to H. Roder et al., Angew. Chem., 96, 895 (1984).

The hydrolysis of the obtained reaction mixture can be effected by means of an acidic aqueous solution, for example by means of a diluted protic acid such as hydrochloric or sulfuric acid in water or by treatment with an aqueous solution of ammonium chloride, preferably at a temperature lower than the room temperature.

The final step of the process which consists in the isomerization of the terminal double bond of the compound obtained by hydrolysis is carried out according to known analogous methods, for example by treating the said compound with an acidic isomerization agent according to the method described for the racemic compound in Swiss Patent No. 537,352 or by treatment with alumina.

The enolate of formula (II) which is used as starting material in the above described process can be readily obtained by treating an ester of cyclogeranic acid of formula

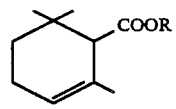

where symbol R designates a linear lower alkyl radical, preferably methyl or ethyl, by means of a strong base such as an alkyl- or a phenyl-lithium. To this effect, n-butyl-lithium is preferred.

The present invention provides also an original process for the preparation of (S)-(—)-alpha-damascone of formula (I), which process can be exemplified by the following reaction scheme:

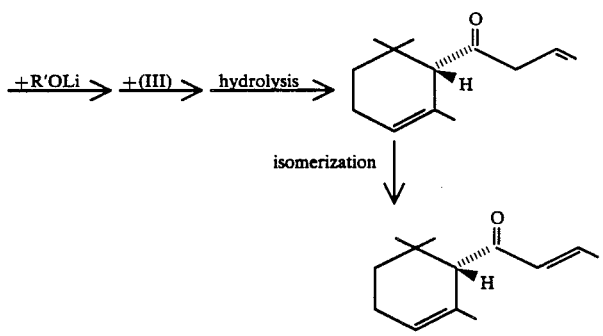

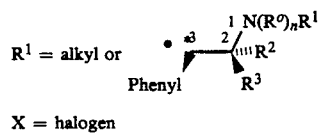

The process consists in three steps carried out subsequently:

a. treatment of an organo-magnesium compound (IV) with at least one equivalent of a lithium alkoxide;
b. addition to the reaction mixture of at least one equivalent of a proton donating chiral reagent consisting of a bifunctional nitrogen derivative of formula (III) as defined above;
c. hydrolysis of the reaction mixture and its isomerization by means of a current isomerizing agent.

Suitable lithium alkoxides include a lithium salt of a lower aliphatic alcohol such as methanol, ethanol, isopropanol or butanol, preferably tert-butanol. Lithium salts derived from chiral anions can also be used to this effect. In this case, lithium derivatives of hydroxy nitrogen compounds of formula (III), wherein Z stands for an OH radical, can be used. Typically, lithium (1R,2S)-2-(N-methyl-N-isopropylamino)-1-phenylpropoxide is employed with success.

Examples of proton donating chiral reagents include bifunctional nitrogen derivatives of formula (III) such as defined above.

By carrying out the first step of the process by means of a lithium salt of a chiral anion, the following step can be effected by employing an achiral proton donor, e.g.

an aliphatic alcohol such as tert-butanol. Therefore, according to a variant of the above described process (S)-(−)-alpha damascone is obtained by:

a'. treating an organo-magnesium compound of formula (IV) with at least one equivalent of a lithium alkoxide consisting of a lithium salt of a hydroxy nitrogen compound of formula (III), wherein Z stands for an OH radical; and b'. adding to the reaction mixture at least one equivalent of a proton donor chosen among aliphatic alcohols, in particular tert-butanol.

The subsequent steps of hydrolysis and isomerization will be carried out as described under letter c. above.

Organo-magnesium compounds of formula (IV) which are used as starting materials in the above described process can be obtained from the corresponding ketene, or 2,6,6-trimethyl-cyclohex-2-enylketene, which compound can be synthesized in accordance with known methods [see J. Org. Chem., 42, 2111 (1977)].

Without being limited by hypothesis on the specific reaction mechanism which governs the invention processes, on the base of the observations accumulated in the course of the different runs carried out in the process development, we have come to the conclusion that the formation of a 1:1 lithium-magnesium mixed complex between the organo-magnesium compound and lithium alkoxide represents a critical step for obtaining a high degree of enantioselectivity.

We have discovered surprisingly that the odor properties of the (S)-(−)-enantiomer of alpha-damascone prepared in accordance with the processes of the invention differ from those of the known racemic derivative. (S)-(−)-alpha-Damascone is characterized by a more pronounced and fresher floral note. Its odor character was reminiscent of rose petals. (S)-(−)-alpha-Damascone possessed moreover a green and slightly winey notes without presenting the "cork" tone and the typical green apple note of the racemic mixture or of the (R)-(+)-enantiomer. By comparison with this latter compound, (S)-(−)-alpha-damascone showed not only marked differences from the qualitative point of view but also it distinguishes itself by an enhanced odor strength and intensity. An evaluation of the respective odor threshold has shown that (S)-(−)-alpha-damascone, with an odor threshold value of 1.5 ppb (parts per billion), is roughly 65 times stronger than (R)-(−)-alpha-damascone having an odor threshold value of 100 ppb. Of course, this fact leads in practice to an increased economy for the consumer; the new compound of the invention can in effect achieve a far superior odor and flavor power than that observed by the utilization of equivalent amounts of the known (R)-(+) enantiomer or racemic mixture.

As a perfuming ingredient, (S)-(−)-alpha-damascone can be used to perfume consumable products as varied as soaps, liquid or solid detergents, fabric softeners or household materials. It can further be employed for the preparation of fragrance compositions destined to fine perfumery. Its use can occur either as an ingredient in its pure concentrated form or, more often, in admixture with other current perfumery coingredients, carriers, excipients or diluents. The man skilled in the art knows by experience that the nature of the coingredients in a given composition depends on the specific odor effect it is desired to achieve. Suitable coingredients can be found in numerous literature sources and they include compounds of natural and synthetic origin.

Concentrations of active (S)-(−)-alpha-damascone can vary in a wide range of values in accordance with the type of application, the nature of the coingredients and that of the consumable material it is desired to perfume. When (S)-(−)-alpha-damascone is used to perfume products such as soaps or detergents, for example, concentrations of the order of 0.1–0.5% by weight based on the total weight of the product it is desired to perfume might be sufficient to confer the desired odor. Concentrations of up to 5% or even higher can be used to prepare perfume compositions or perfume bases.

When used as a flavoring ingredient, (S)-(−)-alpha-damascone develops a floral note. Moreover, it is reminiscent of tea, especially with regard to its herbal character. (R)-(+)-alpha-damascone possesses instead a woody, camphory, dirty and musty taste.

It is interesting to note that (RS)-alpha-damascone develops a fruity aromatic note more pronounced than that of the (S)-(−) enantiomer. Owing to its organoleptic characteristics, (S)-(−)-alpha-damascone is particularly suitable to confer, modify or improve the aromatic properties of foodstuffs and beverages of various nature. It can be used to aromatize infusion or decoction products, bakery products or pastries, jams or even tobacco. The active proportions of (S)-(−)-alpha-damascone in a given flavored material can also vary widely. Depending on the desired effect, one skilled in the art can make an assessment of the most effective values. (S)-(−)-alpha-damascone can be used in admixture with current flavoring ingredients. Suitable ingredients are exemplified in the technical literature [see e.g. S. Arctander, Perfume and Flavor Chemicals, Montclair, N.J. (1969); Fenaroli's Handbook of Flavor Ingredients, 2nd Edition, CRC Press, Inc., (1975)]. The aromatization is usually effected by employing (S)-(−)-alpha-damascone in solution in edible solvents or on supports or carriers. To this effect, ethanol, triacetine, dipropylene glycol or gum arabic and dextrines can be used.

The present invention is illustrated in a more detailed manner by the following examples wherein the temperatures are indicated in degrees centigrade and the abbreviations have the meaning common in the art.

EXAMPLE 1

Process for the preparation of (−)-(1'S,E)-1-(2',2',6'-trimethyl-2'-cyclohexen-1'-yl)-2-buten-1-one a. 150.6 g (0.83M) of methyl alpha-cyclogeranate in 1.5 l of anhydrous tetrahydrofuran (THF) have been treated at −10° with 1.2 equivalents of butyl-lithium. After having left the temperature to raise at about 15°, 1.35 equivalents of allyl-magnesium chloride in THF have been added to the reaction mixture and the resulting mixture has been left at 35° for 30 min.

b. The mixture was then cooled to −10° and, at this temperature, 237 g (1.5 equivalents) of (+)-(4S,5R)-1,5-dimethyl-4-phenyl-2-imidazolidone were added thereto in 1 mn and the mixture has been left for 30 mn at about −10°/0°, whereupon it was poured onto a mixture of NH$_4$Cl-ice. The organic phase after separation was washed with water and a saturated aqueous solution of sodium chloride, dried over anhydrous Na$_2$SO$_4$, filtered and concentrated. The residue was diluted with 30°/50° petrol ether and filtered. The clear filtrate was evaporated and distilled over residue and a fraction having b.p. 50°–70°/10.6 Pa consisting of (−)-(1'S)-1-(2',2',6'- trimethyl-2'-cyclohexen-1'-yl)-3-buten-1-one was collected; [alpha]$^{20}_D$(liquid)=−260°±20°. This fraction was then fractionnally distilled (b.p. 50°-55°/10.6 Pa), treated with alumina according to Reetz et al. [Chem. Ber., 118, 348 (1985)] and redistilled over residue to give a fraction of 89 g of the desired ketone having a purity of 97% as indicated by gas chromatography ([alpha]$^{20}_D$=−280°±20° in CHCl$_3$). By further purification of the obtained product, optically pure (−)-(1'S,E)-1-(2',2',6'-trimethyl-2'-cyclohexen-1'-yl)-2-buten-1-one having [alpha]$^{20}_D$=−509.7° (c=4.0 in CHCl$_3$); m.p.=ca. 27°) was isolated.

By carrying out the reaction as indicated hereinabove and by replacing (+)-(4R,5S)-1,5-dimethyl-4-phenyl-2-imidazolidone by (1R,2S)-2-(N-methyl-N-isopropylamino)-1-phenylpropan-1-ol, the desired product was obtained with an [alpha]$^{20}_D$=−340°±20° (c=6.4; CHCl$_3$) before crystallization.

EXAMPLE 2

Process for the preparation of (−)-(1'S,E)-1-(2',2',6'-trimethyl-2'-cyclohexen-1'-yl)-2-buten-1-one 10 g (66.6 mM) of 2,6,6-trimethyl-cyclohex-2-enylketene [see J. Org. Chem., 42, 2111 (1977)] in 200 ml of anhydrous THF have been treated subsequently with 1.2 equivalents of allyl-magnesium chloride in THF [temp.: −78°→35°; time: 30 mn] and at 20° for 30 mn with 1 equivalent of lithium (1R,2S)-2-(N-methyl-N-isopropylamino)-1-phenylpropoxide [obtained by treating 1 equivalent of (1R,2S)-2-(N-methyl-N-isopropylamino)-1-phenylpropanol with 1 equivalent of n-butyllithium in THF], and finally with 2 equivalents of (1R,2S)-2-(N-methyl-N-isopropylamino)-1-phenylpropanol. The addition of this latter reagent occurs at a temperature of between −50° and −10° during 60 mn. The reaction mixture was poured into an icy aqueous solution of NH$_4$Cl and extracted with ether. The combined organic phases have been treated with a 5% aqueous solution of HCl, and the separated organic phases were washed with ether, treated with a 20% aqueous solution of KOH and extracted with ether to give an ether solution which, upon evaporation, gave (1R,2S)-2-(N-methyl-N-isopropylamino)-1-phenylpropanol.

The mixture of the ketones obtained from the organic extracts was distilled in a bulb apparatus at 70° and 0.5 Torr to give 9.7 g of a product which, by isomerization with alumina according to Reetz et al. [Chem. Ber., 118, 348 (1985)], gave 9.3 g (73%) of (−)-(1'S,E)-1-(2',2',6'-trimethyl-2'-cyclohexen-1'-yl)-2-buten-1-one. [alpha]$^{20}_D$=−396° (c=4.0 in CHCl$_3$). By further purification, the obtained product gave the desired ketone with an [alpha]$^{20}_D$=−488° (c=4.0 in CHCl$_3$; m.p.: 27.5°-28°).

EXAMPLE 3

Measure of the odor threshold

Two samples consisting of (−)-(1'S,E)-1-(2',2',6'-trimethyl-2'-cyclohexen-1'-yl)-2-buten-1-one [or (S)-(−)-alpha-damascone] and of (R)-(+)-alpha-damascone, respectively, were submitted to a group of experts composed of 17 to 20 individuals for organoleptic evaluation.

The two samples were evaluated in accordance with the method described by Guadagni [see Guadagni et al., J. Sci. Food Agric., 14, 761 (1963)]. The concentrations of the samples were set in decreasing order of magnitude so as to diminish the possible errors due to fatigue. The products were evaluated by dissolving them in natural mineral water. Each product was tasted at different dosages by comparison with a sample of water. Three evaluation sessions were effected in a one-week time interval so as to verify the reproducibility of the obtained results. 70% of the correct responses have been considered as meaningful for the assessment of the odor threshold value.

The observed values were the following:
(S)-(−)-alpha-damascone: 1.5 ppb (parts per billion)
(R)-(+)-alpha-damascone: 100 ppb.

EXAMPLE 4

A base perfuming composition of floral type was prepared by mixing the following ingredients (parts by weight):

| | |
|---|---|
| Citronellol | 150 |
| Phenylethanol | 150 |
| Terpineol | 70 |
| Lilial (registered trademark)[1] | 50 |
| Benzyl salicylate | 100 |
| Trichloromethylphenylcarbinyl acetate | 30 |
| Cyclamen aldehyde | 10 |
| Undecylenic aldehyde 10%° | 20 |
| Rose oxide[2] 10%* | 20 |
| Purified indol 10%* | 10 |
| Styrallyl acetate | 10 |
| Linalol | 80 |
| Total | 700 |

[1] L. Givaudan; p-tert-butyl-alpha-methyl-hydrocinnamic aldehyde
[2] Firmenich SA
*in dipropylene glycol The above perfume base was then used to manufacture 4 new compositions by mixing the ingredients indicated below:

| | A | B | C | D |
|---|---|---|---|---|
| Perfume base | 70 | 70 | 70 | 70 |
| Dipropylene glycol | 30 | — | — | — |
| (RS)-alpha-damascone* | — | 30 | — | — |
| (S)-(−)-alpha-damascone* | — | — | 30 | — |
| (R)-(+)-alpha-damascone* | — | — | — | 30 |

*10% solution in dipropylene glycol

These new compositions were then subjected to an odor evaluation by a group of experts. Their comments are given hereinbelow:

Composition A: flat character, without defined rosy smell;

B: pleasant rosy smell, slightly cork note, winey;

C: fresh smell, well-defined rosy character in the direction of rose petals; the most pleasant of the four samples submitted; without secondary unpleasant character, the most powerful;

D: the least interesting sample; marked "cork" note; chemical character.

EXAMPLE 5

Comparative aroma evaluation

A comparative evaluation between the two optically active (R)-(+) and (S)-(−) enantiomers of alpha-damascones have been carried out by a group of experts composed of 10 individuals of both sexes. The two compounds have been tasted in a 1 ppm (part per million) solution of sugar syrup prior diluted to 10%. The two samples were judged as follows:

(S)-(−)-alpha-damascone: woody, herbal, fruity (direction berries), cooked fruit, tobacco, tea, hay, dry leaves;

(R)-(+)-alpha-damascone: hay, camphory, oily, fermented, hazelnut, dirty, without volume.

EXAMPLES 6 TO 10

EXAMPLE 6

A commercial prune concentrated juice was diluted with mineral water and divided into 4 parts of equal volume:

A: non aromatized reference sample;
B: sample to which 0.5 ppm of (RS)-alpha-damascone were added;
C: sample to which 0.5 ppm of (R)-(+)-alpha-damascone were added;
D: sample to which 0.5 ppm of (S)-(−)-alpha-damascone were added.

The four samples thus obtained were subjected to the evaluation of a group of flavor experts who had to express their opinion on their organoleptic properties. Their comments are summarized hereinbelow:

A: typical prune character, rather flat, cooked fruit note;
B: more fruity, juicy and rounded, fermentation character;
C: more woody, dry fruit character, cardboard;
D: even more pronounced dry fruit character, slightly caramel, more fruity; more distinct than B and C; has more character than A with a winey, rum note.

EXAMPLE 7

A commercial concentrated raspberry juice was diluted with mineral water and divided into 4 parts of equal volume. By proceeding as indicated in the example above, three samples containing (RS)-alpha-damascone, (R)-(+)-alpha-damascone and (S)-(−)-alpha-damascone, respectively, were prepared and compared to an unflavored juice sample.

A: typical canned raspberry juice, cooked fruit note, rather flat;
B: hay, camphory, possesses more fruity body, slightly earthy;
C: similar to B, slightly camphory, good fruity note, the "jam" character is reinforced, better than A and B, slightly hay;
D: more fruity, cooked fruit, more juicy and jammy, more typical berry, woody; more typical raspberry; this sample was preferred since its note was the nearest to the natural notes of raspberry.

EXAMPLE 8

100 ml of acidic sugar syrup were prepared by dissolving 8 g of sugar and 0.1 g of citric acid in mineral water. The solution thus obtained was flavored with a concentrated strawberry flavor at a dosage of 0.05% by weight (origin: Firmenich SA) whereupon it was divided into 4 parts of equal volume. By operating as indicated in the above examples, the three samples of alpha-damascone under examination were evaluated at a concentration of 0.03 ppm. The comments of the flavor experts are summarized hereinbelow:

A: fruity, strawberry jam, buttery;
B: possesses more body than A, camphory, hay, fermented;
C: more fruity than A and B, more marked jam character, cooked fruit;
D: the most fruity, possesses a more marked character of red berries, more defined jam character; D is the preferred sample.

EXAMPLE 9

6 g of Ceylon tea leaves were used to prepare an infusion product by suspending them into 800 ml of boiling water. As indicated in the above examples, the infusion was divided into 4 equal parts and the three samples of alpha-damascone were compared at a concentration of 0.25 ppm with an unflavored control tea sample.

A: unflavored tea beverage
B: more fruity, apricot note, more floral, earthy; the odor has more impact than that of unflavored sample A;
C: floral, more marked dry leaves character, slightly earthy, nutty; similar to sample A but possesses more flavor and impact;
D: more marked aromatic tea character, dry leaves, hay, more fruity and sweeter; sample D is preferred, it shows the most typical black tea character.

EXAMPLE 10

A sample consisting of brand cigarettes manufactured with flue-cured tobacco was used for carrying out this evaluation.

Three samples were flavored by the injection of a 95% ethanol solution of the three damascones under examination. As indicated above, sample A is the control unflavored cigarette, sample B was flavored with (RS)-alpha-damascone, sample C with (R)-(+)-alpha-damascone and sample D with (S)-(−)-alpha-damascone, each at a dosage of 12.5 ppm by weight based on the total weight of the tobacco. The samples were preconditioned by storing them during 48 hours.

The smoke evolving by combustion of the cigarette samples under examination was evaluated organoleptically by a panel of flavor experts. By comparison, the odor perceived while opening the cigarette package is also indicated.

Odor at the opening of the package:
A: neutral, woody;
B: fruity, slightly caramel, woody, fermented, more pronounced tobacco note;
C: good tobacco head note, fruity, fermented, slightly floral;
D: richer tobacco note, more fruity, more marked hay character.

Smoke aroma:
A: typical tobacco note;
B: fuller character, more fruity, heavy, dirty after-taste;
C: lighter, more herbal, hay, sweeter, more pronounced flue-cured character;
D: richer, more pronounced tobacco character, more fruity, dry fruit type, than C, sweeter than A, possesses more body.

What we claim is:

1. Method to confer, modify or improve the organoleptic properties of foodstuffs, beverages and infusion or decoction products, which comprises the step of adding thereto a flavor effective amount of (−)-(1S)-1-(2',2',6'-trimethyl-2'-cyclohexen-1'-yl)-2-buten-1-one.

2. Method to confer, modify or improve the odorous properties of products comprising perfumes, perfume bases or consumable materials which comprises the step of adding thereto a fragrance effective amount of (−)-

(1S)-1-(2',2',6'-trimethyl-2'-cyclohexen-1'-yl)-2-buten-1-one.

3. The method according to claim 2, wherein the consumable material is a soap, a solid or liquid detergent, a fabric softener or an air or body deodorizer.

4. The method according to any of claims 1 to 3, wherein (−)-(1S)-1-(2',2',6'-trimethyl-2'-cyclohexen-1'-yl)-2-buten-1-one is accompanied by minor amounts of (+)-(1R)-1-(2',2',6'-trimethyl-2'-cyclohexen-1'-yl)-2-buten-1-one.

5. The product produced by the method of claim 1, 2 or 3.

6. The product of claim 5 wherein the (−)-(1S)-1-(2',2',6'-trimethyl-2'-cyclohexen-1'-yl)-2-buten-1-one is accompanied by minor amounts of (+)-(1S)-1-(2',2',6'-trimethyl-2'-cyclohexen-1'-yl)-2-buten-1-one.

7. A composition comprising a flavored foodstuff or beverage which includes a flavor effective amount of (−)-(1S)-1-(2',2',6'-trimethyl-2'-cyclohexen-1'-yl)-2-buten-1-one.

8. A composition comprising a flavored infusion or decoction product which includes a flavor effective amount of (−)-(1S)-1-(2',2',6'-trimethyl-2'-cyclohexen-1'-yl)-2-buten-1-one.

9. The composition of claim 8 wherein the infusion or decoction product comprises one of tea or tobacco.

10. A composition comprising a consumable material which includes a fragrance effective amount of (−)-(1S)-1-(2',2',6'-trimethyl-2'-cyclohexen-1'-yl)-2-buten-1-one.

11. The composition of claim 10 wherein the consumable material comprises one of a detergent, a fabric softener, an air deodorizer or a body deodorizer.

12. A composition comprising a perfume or perfume base which includes a fragrance effective amount of (−)-(1S)-1-(2',2',6'-trimethyl-2'-cyclohexen-1'-yl)-2-buten-1-one.

13. The composition according to any of claims 7 to 12 wherein the (−)-(1S)-1-(2',2',6'-trimethyl-2'-cyclohexen-1'-yl)-2-buten-1-one is accompanied by a minor amount of (+)-(1S)-1-(2',2',6'-trimethyl-2'-cyclohexen-1'-yl)-2-buten-1-one.

14. A composition of a flavored foodstuff or beverage which includes a flavor effective amount of a flavoring ingredient consisting of (−)-(1S)-1-(2',2',6'-trimethyl-2'-cyclohexen-1'-yl)-2-buten-1-one.

15. A composition consisting of a flavored infusion or decoction product which includes a flavor effective amount of a flavoring ingredient consisting of (−)-(1S)-1-(2',2',6'-trimethyl-2'-cyclohexen-1'-yl)-2-buten-1-one.

* * * * *